United States Patent [19]

Holzer

[11] Patent Number: 5,026,343

[45] Date of Patent: Jun. 25, 1991

[54] DEVICE FOR NEEDLELESS HYPODERMIC INJECTION OF MEDICATIONS

[76] Inventor: Walter Holzer, Drosteweg 19, D-7758 Meersburg, Fed. Rep. of Germany

[21] Appl. No.: 438,729

[22] Filed: Nov. 17, 1989

[30] Foreign Application Priority Data

Nov. 21, 1988 [DE] Fed. Rep. of Germany ....... 3839287
Jan. 20, 1989 [DE] Fed. Rep. of Germany ....... 3901691

[51] Int. Cl.$^5$ ............................................. A61M 5/30
[52] U.S. Cl. ......................................... 604/68; 604/72; 604/135
[58] Field of Search ................... 604/68-72, 604/132, 135

[56] References Cited

U.S. PATENT DOCUMENTS 3,131,692  5/1964  Love ................................. 604/68
3,308,818  3/1967  Rutkowski ...................... 604/69
3,788,315  1/1974  Laurens .......................... 604/70

FOREIGN PATENT DOCUMENTS 1082373  5/1960  Fed. Rep. of Germany ........ 604/68
1329086  4/1963  France ............................. 604/70

Primary Examiner—Stephen C. Pellegrino

[57] ABSTRACT

An ampoule is provided with openings and a flexible membrane, forming a cavity, in which medication is stored in liquid form. The membrane is extended into the front end of an injection pistol which has a spring loaded punch which upon release, empties the ampoule through the openings. The ampoule has a flat front plate which covers the front end of the injection pistol. The openings of the ampoule are formed as nozzles in short truncated cones arranged in circular fashion on the front plate.

11 Claims, 3 Drawing Sheets

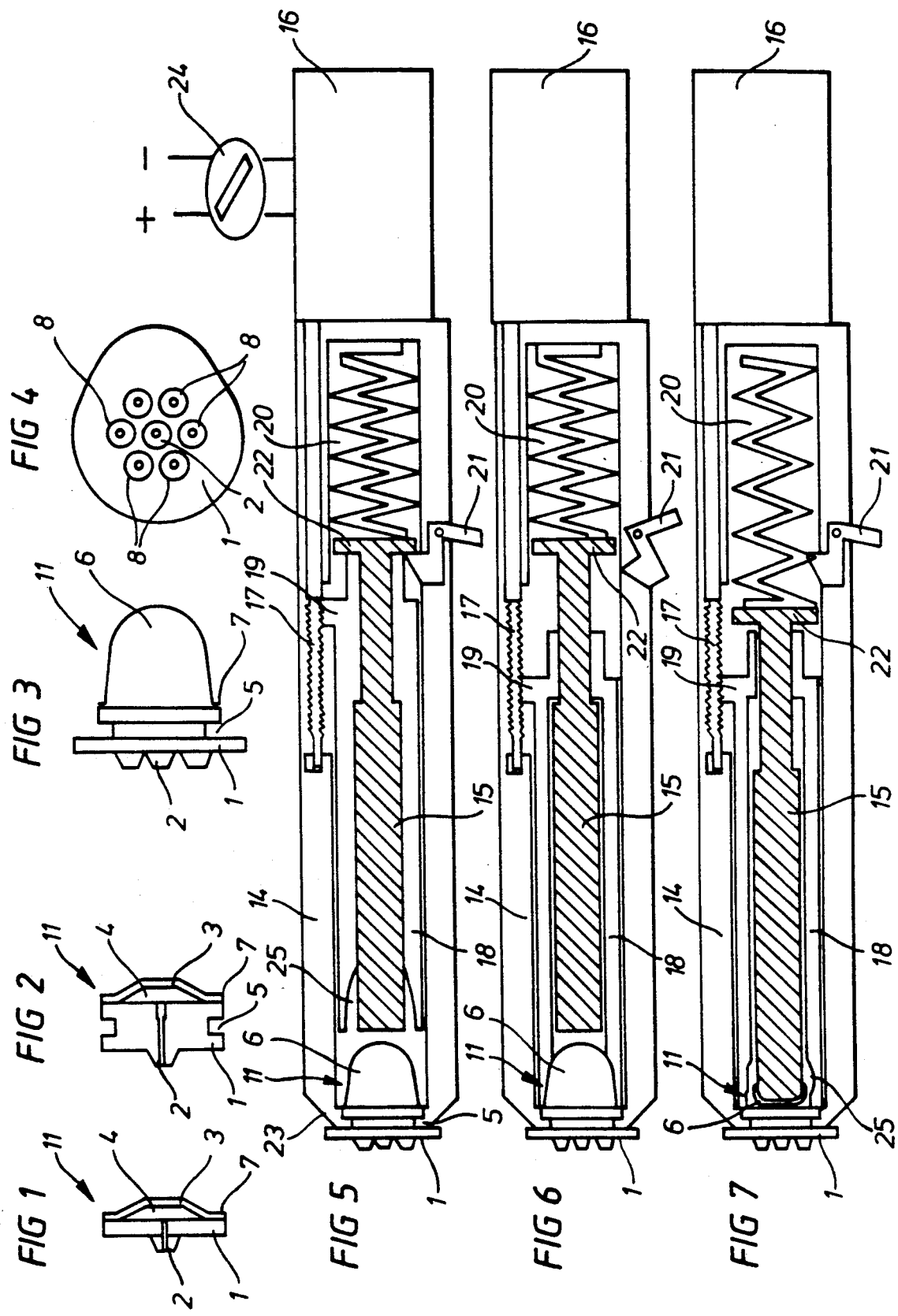

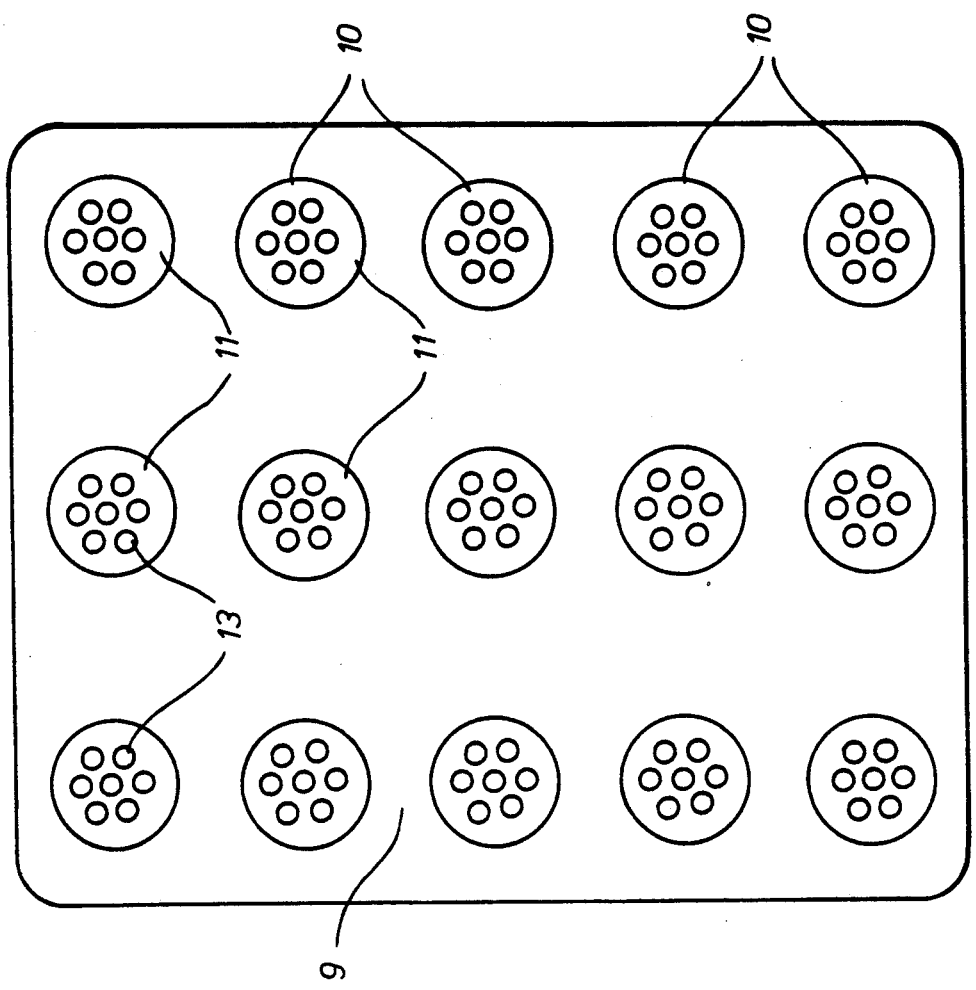
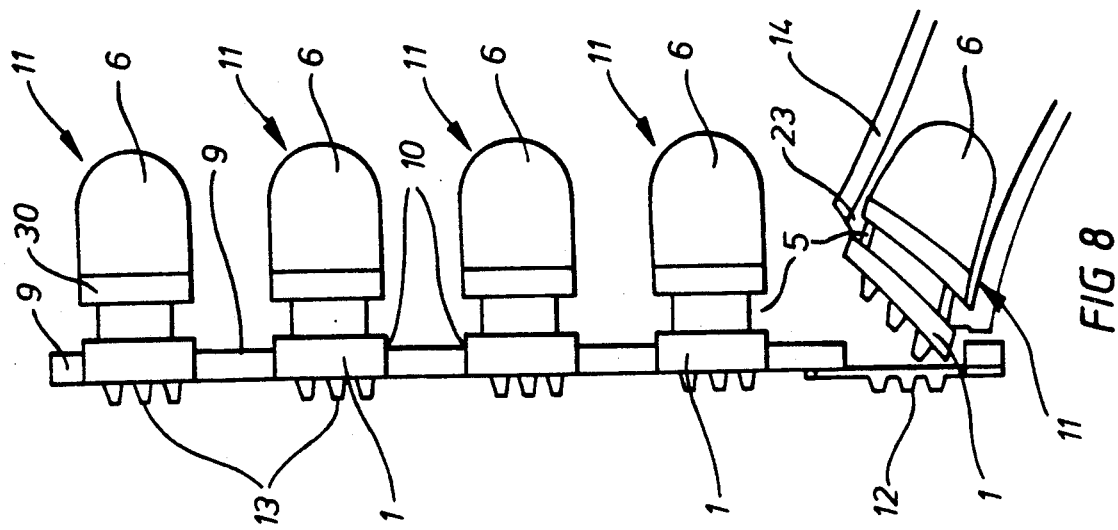

DEVICE FOR NEEDLELESS HYPODERMIC INJECTION OF MEDICATIONS

BRIEF SUMMARY OF THE INVENTION

The invention concerns the needleless hypodermic injection of medications, by means of an ampoule having holes and a flexible membrane, forming a cavity holding medication in liquid form. The ampoule is stretched in a hypodermic pistol, in the cocking of the pistol, the pistol having a spring loaded punch which upon discharge of the pistol engages the membrane and forces the medication through the holes.

The device is especially useful and effective for performing a large number of vaccinations in a short period of time.

Patent DE-OS 1 491 695 shows an ampoule for needleless injection, but the ampoule therein has only one opening and the device in being emptied could possibly injure the skin.

Another patent, DE OS 1 907 296, also for needleless injection, includes several holes through which the medication is simultaneously ejected. However, in the latter instance the holes are formed in outwardly directed sharp needle points, so that the mere pressing of the ampoule to the skin can injure it. Additionally, in that device, there exists a danger because of the numerous needle-shaped holes in the ampoule, the front surface of the ampoule is positioned obliquely across the injection location, so that the simultaneous ejection of the medication through all of the holes of the ampoule cannot be guaranteed.

An object of the present invention is to provide a device for needleless hypodermic injection, wherein in the operation thereof the injection is facilitated, and it is assured that the ampoule is placed with its front or effective surface on the injection location in a constantly repeatable manner, and the holes of the ampoule are positioned evenly at the intended location on the skin.

A more specific object is to provide a device of the character referred to, capable of carrying out the intended function, wherein the ampoule includes a flat front plate which covers the front effective surface of the injection pistol utilized, and in which the holes of the ampoule are formed as in nozzles in flat, short truncated cones, and in which these holes are arranged in a circular pattern.

An additional advantage lies in the specific construction wherein because of the flat front plate referred to, the openings lie evenly on the skin of the patient in a constantly repeatable manner.

A further advantage exists in the specific construction in that the user need only to ascertain that the front plate lies on the skin, and the necessary consequence is that the holes in the ampoule inject the medications evenly into the location of the injection.

In previously known devices, there was always the danger that the ampoule would be held in an improper oblique position so that the medication would often be ejected inaccurately, or even be discharged sideways. Additionally in the use of a plurality of needle-sharp nozzles there is always the danger that the skin would be harmed merely by applying the nozzles to the skin.

A still further advantage is accomplished by the specific construction wherein the ampoule has a front plate at the front forming a shield, and the front plate can be placed on the skin at the location of the injection with a large surface engaging the skin, whereby it is assured that the flat, short nozzles provided, evenly contact the skin.

An another object of the invention is to provide another advantage, by means of a specific construction which includes a front plate and means for mounting a flexible membrane thereon, in such a way that the membrane forms a bellows utilized in injecting the medication.

Still another advantage is provided in a specific mechanical construction of an ejection pistol, for mounting the ampoule therein for performing the injection operation, wherein the pistol has a cavity receiving the bellows and confining it whereby in the striking of the bellows by a driving punch in the discharge of the pistol, the membrane is protected.

Another advantage is to provide means for coding the active substances in the ampoules in a recognizable manner, such as by either color or texture.

BRIEF DESCRIPTION OF THE SEVERAL VIEWS OF THE DRAWINGS

FIGS. 1–4 show different forms of ampoules embodying the features of the invention.

FIGS. 5–7 show an arrangement of an ampoule in an injection pistol, in different phases of operation of the pistol.

FIGS. 8 and 9 show devices forming storage means for the ampoules.

DETAILED DESCRIPTION

Figure 12:
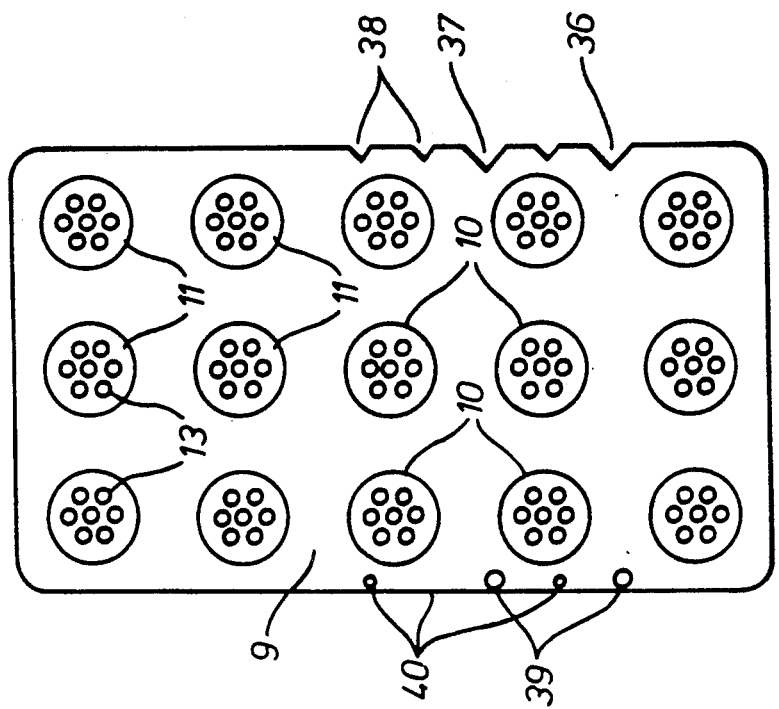
FIG. 12 shows a storage device or plate having an additional arrangement of coding elements.

FIGS. 1 and 2 show the device of the invention in its simplest forms. In these figures an ampoule is shown, which includes only a front plate 1 and a membrane 3. The front plate is provided with a nozzle 2 and the membrane 3 is flexible, holding medication at 4 in the form of a liquid.

FIG. 3 shows an additional form of the device of the invention, including a front plate 1 and a large membrane 6 forming a roll bellows. The front plate is essentially larger in diameter than the bellows, the latter being bound at the edge 7 of the front plate by means of welding or glue.

FIG. 4 shows the device of FIG. 3 from left of the latter. The front plate 1 in this case (FIGS. 3, 4) includes six nozzles 8 which are arranged in a circular pattern around the central nozzle 2, the latter being incorporated in the forms of FIGS. 1, 2.

FIGS. 8 and 9 show a form of plate 9 having a plurality of mounting holes 10, in this case fifteen in number, in which the ampoules 11 are inserted and supported.

The plate 9, has on its front side (left side, FIG. 8) a film 12 which is applied to the plate by vacuum. The film covers the plate itself and the ampoules 11, and the film holds the ampoules firmly in place and closes and covers the nozzles 13.

The ampoules are removed or released from the plate, as indicated at the bottom of FIG. 8, and following that removal, the film 12 remains in place on the plate 9, as shown in FIG. 8 and does not disturb or interfere with any additional steps in the operation or use of the device. The plate 9 serves as a storage device, holding the ampoules until they are used. The ampoule is removed by means of the pistol itself (14) by applying the front end of the pistol to the ampoule, by inserting elements 23 of the pistol into the circumferential groove 5, whereby the ampoule is taken off by a light tilting motion. This removes the ampoule from the hole in the plate, and from the film, the latter remaining in place on the plate.

An important feature of the invention resides in the injection pistol which is shown in different phases or positions in FIGS. 5-7. In FIG. 5 the pistol 14 is in cocked condition. A punch 15 is slidable in a casing 18 which is also slidable, the punch in this cocked position being in a rear position to which it is moved by a driving motor 16. A spindle 17 is driven by the motor and is provided with threads, and serves to move the casing 18 rearwardly by means of cooperating threads 19. This moves the casing 18 against the compression spring 20 and moves the spring plate 22, on the punch 15, therewith, and the punch/plate compresses the spring 20 to a position in which the trigger 21 engages the spring plate 22, cocking the pistol. The ampoule 11 is held in the forward end of the pistol by means of elements 23 in the groove 5, acting as gripper or uptake elements.

Reference is now made to FIG. 6 showing the pistol still in cocked position, but with the casing 18 in a forward position. In the step of cocking the pistol as described in connection with FIG. 5, the casing 18 was moved rearwardly by the driving motor 16. After the pistol is cocked in this manner, the driving motor is reversed, through a reversing switch 24, and the driving motor, acting through the spindle 17, drives the casing 18 forwardly (to the left, FIG. 6). The casing 18 at its forward end has a predetermined shaped cavity 25 for receiving the membrane or roll bellows 6, and thereby prevents bursting of the bellows or any other part of the ampoule by the punch 15. The trigger 21 is released or pulled, shown in such released position in FIG. 6, and the spring 20 drives the punch 15 forwardly in a fast action. In this step, the punch 15 engages the membrane or bellows 6, and therethrough engages the ampoule, as shown in FIG. 7. In this action, the roll bellows 6, under the pressure of the punch 15 has been rolled in, substantially eliminating the cavity previously formed therein. The driving motor 16 is now again reversed by means of the switch 24 and it brings the punch 15 and casing 18 rearwardly to the position shown in FIG. 5, and the ampoule 11 can now be removed from the pistol and a new one taken from the storing plate 9 and utilized in the pistol.

The specific constructions and arrangements illustrated and described above are to be understood only as schematic; for example the reversing switch 24 could be a combination of end switches and automatic ejection of the used ampoule can be provided according to the invention. Thus, the examples presented are not to be considered as limiting.

Figure 11:
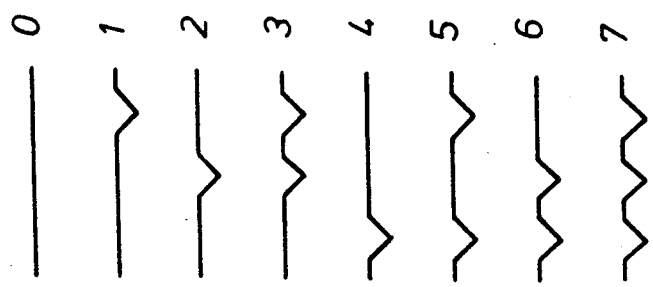
FIG. 11 shows an arrangement of different permutations of coding elements.

In certain cases, such as for use of the device by diabetics, an advantage is produced by providing a coding arrangement. In such use of the device, it is ordinarily necessary to inject doses of different values, and convenient to provide codes indicating different values, such as 1, 2, 4, 8, 16, 24, 32, and 40 units. A number of ampoules, such as eight can be digitally numbered with notches, as shown in FIG. 11. These notches may be formed in the front plate 1 of the ampoule, as shown in FIG. 10.

By utilizing different numbers of notches, to six places or positions, it is also possible not only to provide a code for numbering, but also digitally coding the number of the units in a single ampoule. The coding shown in FIG. 10 includes a digital indication at the first position by the notch 36, and at the third position the notch 37 would indicate a unit count of one plus four, that is, five units. The small notches 38 serve as orientation aids in applying the device to the skin.

In a similar manner, coding notches, such as 36, 37, can also be applied to the rim of the plate 9 as shown in FIG. 12, in order to identify the contents of the whole package that is constituted by the plate and the ampoules.

Figure 10:
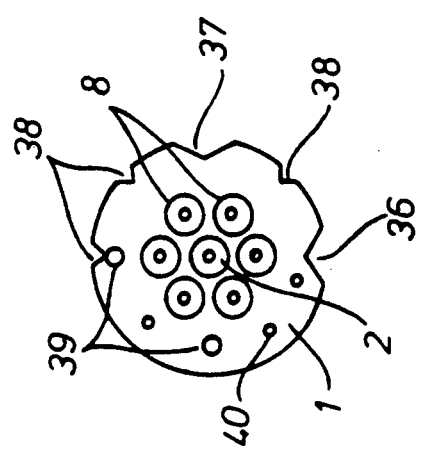
FIG. 10 shows an arrangement of codings on the front plate of the ampoule.

Coding elements 39, 40, are in elevated form, in FIGS. 10 and 12, and these serve the same purpose as the notches 36, 37, 38, but being raised are in the form of traditional braille.

The device of the invention is not necessarily limited to the devices here shown, but the invention in its broad scope covers applying the features to ampoules currently in use.

The coding step can also be used to indicate color. Because of limitations to black and white in the drawings, it is pointed out that color may be utilized, for example in color coding the plate 9 to indicate ampoules according to FIGS. 1-4, or coloring the plate 9 of FIGS. 8, 9, 12, in corresponding colors.

It is also possible within the scope of the invention to provide computer-readable bar code or other common coding devices, in the device.

The device eliminates not only human error in the scoring of doses, but also simplifies the operation and increases the security against mistakes, when used by the sick. Neither the color coding nor the coding with notches or similar indicators, would entail substantial manufacturing costs.

I claim:

1. A device for needleless hypodermic injection of medications by means of and injection an ampoule (11) pistol means (14) and, the ampoule including a front plate (1) having openings (2, 8) therethrough and a flexible membrane (3, 6), the ampoule forming a receptacle (4) having a cavity between the membrane and front plate, and the ampoule having a liquid medication in the cavity, the ampoule being mounted in the front end of the injection pistol with its membrane extended into the pistol means, the pistol means having a spring loaded punch (15) driven abruptly forwardly in response to which the punch engages the membrane and drives the medication through the openings,
   wherein,
   the front plate (1) of the ampoule (11) extends across and covers the front end of the pistol means (14), the device being applied to the skin of a patient by applying the front plate to the skin at an injection location, the openings (2, 8, 13) are formed in flat, tuncated cones arranged in circular formation on the front surface of the front plate.

2. A device according to claim 1 wherein,
   the front plate (1) is enlarged and is made of firm synthetic material.

3. A device according to claim 1 wherein,
   the ampoule (11) has a circumferential groove (5) rearwardly of the front plate forming a circumferential support rearwardly of the groove, and
   the membrane (6) forms a roll bellows having a rim (7), and that rim is secured to the support.

4. A device according to any of claims 1-3 wherein,
the pistol means (14) includes a claw-shaped griper (23) adjacent its front end capable of releasably holding the ampoule and thereby so mounting the ampoule,
the pistol means includes a casing (18) within the gripper and having a recess (25) adjacent its front end and adjacent the front end of the piston means, the recess corresponding to the shape of the membrane and receiving the membrane, the punch (15) being slidable in the casing and capable of striking the membrane and the casing by means of the position of the membrane in the casing preventing bursting of the membrane by the punch.

5. A device according to claim 1 in combination with a storage member, wherein,
the storage member includes a mounting plate (9) having a front side and mounting holes (10) therein,
the ampoules (11) are mounted in the mounting holes, the front plates (1) of the ampoules have front surfaces lying substantially at the front surface of the mounting plate, and
a film (12) is adhered to the front surface of the mounting plate, securing the ampoules in the mounting holes and closing the openings (2, 8, 13) of the ampoules.

6. A device according to claim 1 wherein,
the injection pistol means (14) includes a driving motor (16) operable for retracting the punch (15) and thereby cocking the pistol.

7. A device according to claim 1 wherein,
each ampoule (11) is recognizably color coded as to contents and active substance.

8. A device according to claim 1 wherein,
each ampoule (11) is texture coded by means of notches (36, 37, 38) as to contents and active substance.

9. A device according to claim 1 wherein,
each ampoule (11) is texture coded in braille, by means of raised elements (39, 40).

10. A device according to claim 1 wherein,
each ampoule (11) is texture coded, the texture coding giving digital information on concentration, amount and/or active substance units.

11. A device according to claim 1 wherein,
the ampoules (11) are mounted in a mounting plate (9), forming a package, and
the ampoules and the mounting plate of the package are provided with the same coding which may be one of color coding, texture coding.

* * * * *